(12) United States Patent
Gorsuch et al.

(10) Patent No.: US 6,802,820 B1
(45) Date of Patent: Oct. 12, 2004

(54) SPECIALIZED HOLLOW FIBER MEMBRANES FOR IN-VIVO PLASMAPHERESIS AND ULTRAFILTRATION

(75) Inventors: Reynolds Gorsuch, Yountville, CA (US); Henry Grage, Danville, CA (US)

(73) Assignee: Transvivo, Inc., Napa, CA (US)

( * ) Notice: Subject to any disclaimer, the term of this patent is extended or adjusted under 35 U.S.C. 154(b) by 0 days.

(21) Appl. No.: 09/549,131

(22) Filed: Apr. 13, 2000

(51) Int. Cl.[7] .......................... A61M 1/34; B01D 61/14; B01D 69/08
(52) U.S. Cl. .................... 604/6.04; 604/4.01; 604/5.01; 604/5.04; 604/6.01; 604/6.09; 604/28; 604/27; 210/650; 210/500.23
(58) Field of Search ............................... 604/4.01, 5.01, 604/5.04, 6.01, 6.04, 6.09, 27, 28; 210/650, 651, 500.23

(56) References Cited

U.S. PATENT DOCUMENTS

| | | | |
|---|---|---|---|
| 4,832,034 A | 5/1989 | Pizziconi et al. | 128/632 |
| 4,882,223 A | * 11/1989 | Aptel et al. | 210/500.22 |
| 4,935,141 A | * 6/1990 | Buck et al. | 210/500.38 |
| 4,950,224 A | 8/1990 | Gorsuch et al. | |
| 5,145,583 A | 9/1992 | Angleraud et al. | 210/646 |
| 5,151,082 A | 9/1992 | Gorsuch et al. | |
| 5,152,743 A | 10/1992 | Gorsuch et al. | |
| 5,224,926 A | 7/1993 | Gorsuch et al. | |
| 5,605,627 A | 2/1997 | Carlsen et al. | 210/321.79 |
| 5,735,809 A | 4/1998 | Gorsuch et al. | |
| 5,980,478 A | 11/1999 | Gorsuch et al. | |

FOREIGN PATENT DOCUMENTS

| | | |
|---|---|---|
| EP | 0 801 973 A1 | 10/1997 |
| EP | 0 882 494 A1 | 12/1998 |
| FR | 2566 003 | 12/1985 |
| JP | 9323031 | 12/1997 |

* cited by examiner

*Primary Examiner*—John Kim
(74) *Attorney, Agent, or Firm*—Knobbe, Martens Olson & Bear, LLP

(57) ABSTRACT

An in-vivo plasmapheresis and/or in-vivo ultrafiltration membrane comprises a plurality of elongated hollow fibers each fiber having an interior lumen extending along the fiber length, the fiber wall having a plurality of zones between the inner and outer wall surfaces, each of the zones having a mass density different than the mass density of an adjacent zone. The fiber wall is characterized by having a lower mass density zone at the inner wall surface and a higher mass density zone at the outer wall surface.

24 Claims, 7 Drawing Sheets

SEM OF SECTION ZONE 1 PORE STRUCTURE

SEM OF FIBER CROSSECTION SECTION ZONES 1,2 AND 3

FIG. 5 SEM OF CROSSECTIONS ZONES 3 AND 4

SPECIALIZED HOLLOW FIBER MEMBRANES FOR IN-VIVO PLASMAPHERESIS AND ULTRAFILTRATION

BACKGROUND OF THE INVENTION

In U.S. Pat. Nos. 4,950,224, 5,152,743, 5,151,082, 5,735,809 and 5,980,478 there are disclosed methods and apparatus for carrying out in-vivo plasmapheresis for separating plasma from other blood components within the body and blood vessels of the patient. The apparatus uses pumping means to create a trans-membrane pressure (TMP) and motivate the flow of fluid from within the in-vivo system, whereby blood plasma is pumped from the patient to a treatment means such as a dialyzer apparatus in which toxic metabolic waste in the plasma is removed. After the plasma is treated for removal of waste products, excess fluids, toxins, and/or other deleterious plasma proteins, the treated plasma is returned and reintroduced to the patients' blood stream. Such methods are referred to as plasma dialysis, ultrafiltration or blood purification. The methods and apparatus described in the aforesaid patents are incorporated herein by reference.

These methods of toxin removal from blood as taught by the above patents are unique and substantially superior from conventional means of hemodialysis as presently practiced for both acute and chronic kidney failure, primarily because removal of whole a blood from the patient's vasculature is eliminated from the procedure using plasma, or portions of the plasma instead. In conventional hemodialysis procedures hollow fiber membranes are used in the ex-vivo dialysis and hemofilter cartridges for blood purification. The blood is routed from the body through the center lumen of the hollow fibers in the cartridges and dialysate fluid is routed over the outside walls of the fibers within the cartridge cavity in counter-flow direction to blood flow. Thus, toxin diffusion and ultrafiltration are from inside the fiber lumen to a compartment outside the fiber walls where the ultrafiltrate and toxin-saturated dialysate are collected for further processing and/or disposal.

Conventional hollow fiber membranes commercially used for present hemodialysis, hemo-ultrafiltration, and dialyzer cartridges fabricated from proprietary and non-proprietary polymer compositions generally utilize two types of morphologies: symmetrical and asymmetrical. In a symmetrical composition, the basic morphology or cellular structure and porosity of the fiber wall is uniform from the inner lumen to the outside surface. In asymmetrical compositions, both morphology and pore structures vary from the inner lumen to the outer surface to meet the high pressure requirements of the filter cartridges in which the TMP inside the fiber lumen is high (100–300 mmHg) while the blood flow itself in the fibers is near stagnant (2–300 ml/min/7,000 fibers= 0.042 ml/fiber). These commercial membranes generally also have poor structural strength, acceptable in an encapsulated device external to the body but which would not be acceptable for an in-vivo placement for safety reasons. Such conventional fiber membranes are not suitable for the demanding environment of the in-vivo, high blood flow (vena cava=2.5 1/min), low TMP ($\leq$50 mmHg), and unencapsulated environment of plasma extraction devices described by the aforesaid patent applications.

SUMMARY OF THE INVENTION

The present invention is directed to specialized hollow fiber membranes having the function of separation of plasma or a portion of the plasma from blood and having the unique morphology, performance properties and materials biocompatible characteristics necessary for effective and optimal utilization for in-vivo vascular implantation as the operating element in catheter-based devices as described in the aforesaid patents and other such similar devices for the separation and extraction of plasma and plasma components from the blood. The ultrafiltrate (exudate) may be transported ex-vivo via a catheter lumen where it is discarded, or treated by cascade filtration means, dialysis (solute diffusion) means, or other methods known to the art, and returned to the patient via a separate lumen in the catheter.

The hollow fiber membrane of the invention is tubular in shape and generally circular in cross-section, having a coaxial inner lumen along the length of the fiber in its center. The wall volume of the fibers is asymmetrical with a variable morphology from the outer diameter to that of the inner diameter, having a higher mass density at the outer wall and a lower mass density at the inner wall. The fibers are designed to facilitate ultrafiltration with the permeate outside the fibers and the exudate inside the fibers. The inner lumen of all fibers in a fiber extraction assembly are in direct fluid communication with the access lumen of the catheter which provides means for transporting the exudate ex-vivo.

DETAILED DESCRIPTION OF THE PREFERRED EMBODIMENT

As illustrated in FIGS. 1–5, the features of the fiber wall of the membrane of the invention include a pore and void structure defined within frames or solid walls which form boundaries of the pores. The pores are voids of variable definitive sizes which permit passage of fluid through the fiber wall to the lumen and which pores obstruct the passage of components larger than the pore diameter. As illustrated particularly in FIG. 3, the pores are irregular-shaped voids bounded by solid frames to form irregular tortuous paths for irregular and regular-shaped solutes. The wall structure of the fiber from the outer surface to the lumen is a continuum with non-linear pore and void distribution. The resulting structure is a continuous change in mass density between the outer surface of the fiber and the inner lumen surface. Thus, it is convenient to describe these changes in mass density as sections of the wall area having an average nominal pore size, porosity and wall mass in terms of zones with macro functions.

Figure 1:
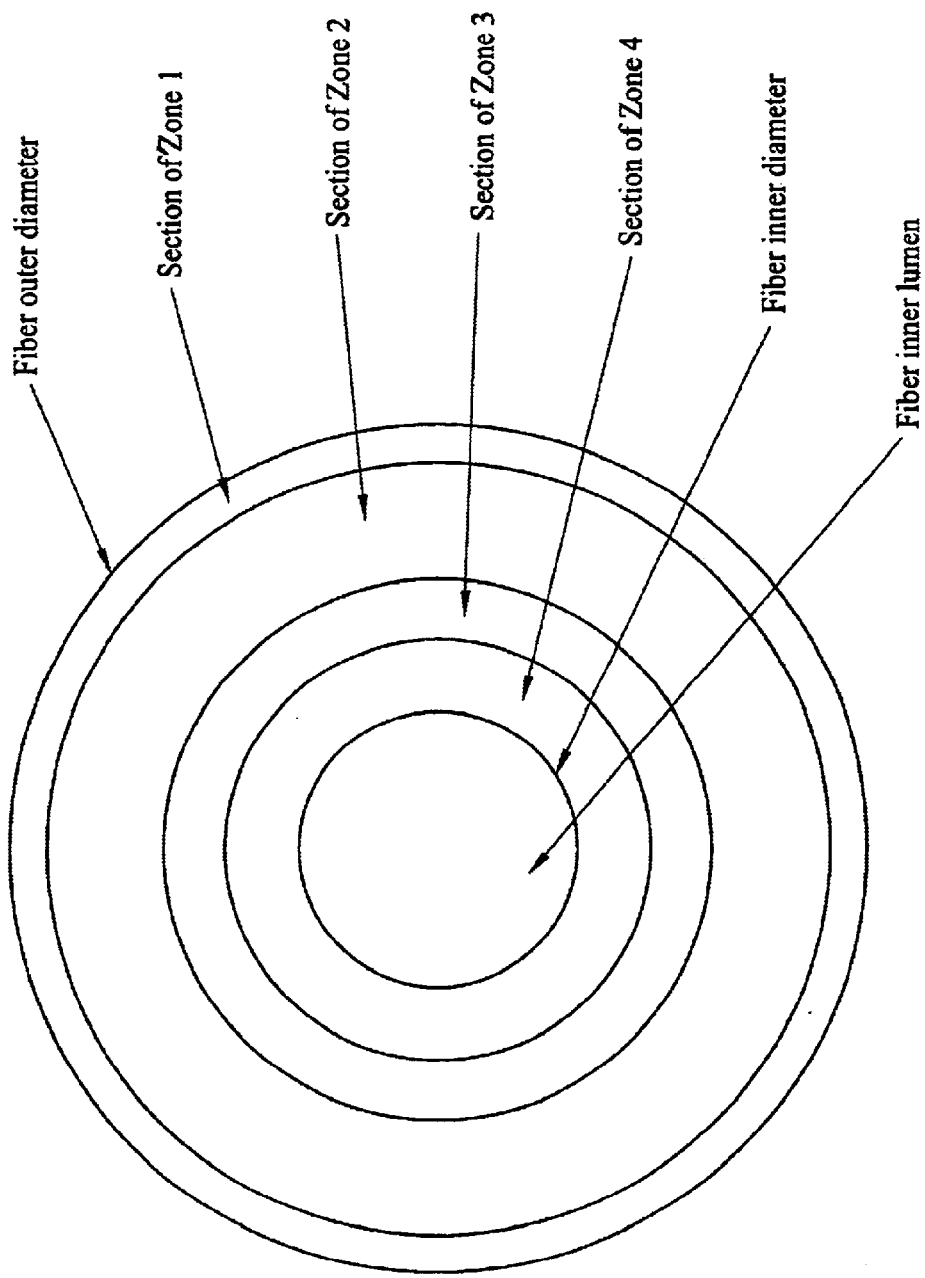
FIG. 1 is a schematic end view of a hollow fiber illustrating the membrane morphology structure having four zones.

In FIG. 1, the wall structure illustrated has four zone sections, each zone characterized by a different mass pore density based on the average nominal pore size in the respective zones. The section of Zone 1 is adjacent to the fiber outer surface or outer diameter. Zone 1 forms the fiber interface with the permeate blood flow and although being the thinnest zone contains the highest density of operationally controlling pores for the fiber membrane performance. Thus, Zone 1 has the principal effect in the filtration process for controlling the trans-membrane flux (TMF) which is dependent on pore size, porosity and virtual membrane thickness.

The section of Zone 2, while having some flux-controlling pores, is principally a structural member for providing strength to the fiber as well as acting as a conduit for exudate flow to the section of Zone 3. The latter is principally a structural member with expanded pores for reducing the hydraulic resistance and providing a fluid conduit to the lumen of the fiber, and thus, in the example, as shown, has little filtration function. The section of Zone 4 has very large voids and pores with very little solid structure, thereby having the primary function of a major reduction of hydraulic resistance through the membrane and defining the fiber inner lumen diameter surface.

Figure 2:
FIG. 2 is a scanning electron microscopy (SEM) image of a cross-section of a portion of the fiber of the invention at 400 $\mu$m magnification showing four zones of the asymmetrical wall structure between the inner and outer fiber wall surfaces.

FIG. 2 illustrates a cross-section of the fiber wall showing the structure of Zones 1–4 at 400 $\mu$m magnification. The fiber wall morphology demonstrates the continuum of expanding plurosity and open spaces from the virtual control pore size of Zone 1 adjacent to the outer fiber diameter to the very open and low-flow resistant structure in Zone 4 adjacent to the inner lumen wall.

Figure 3:
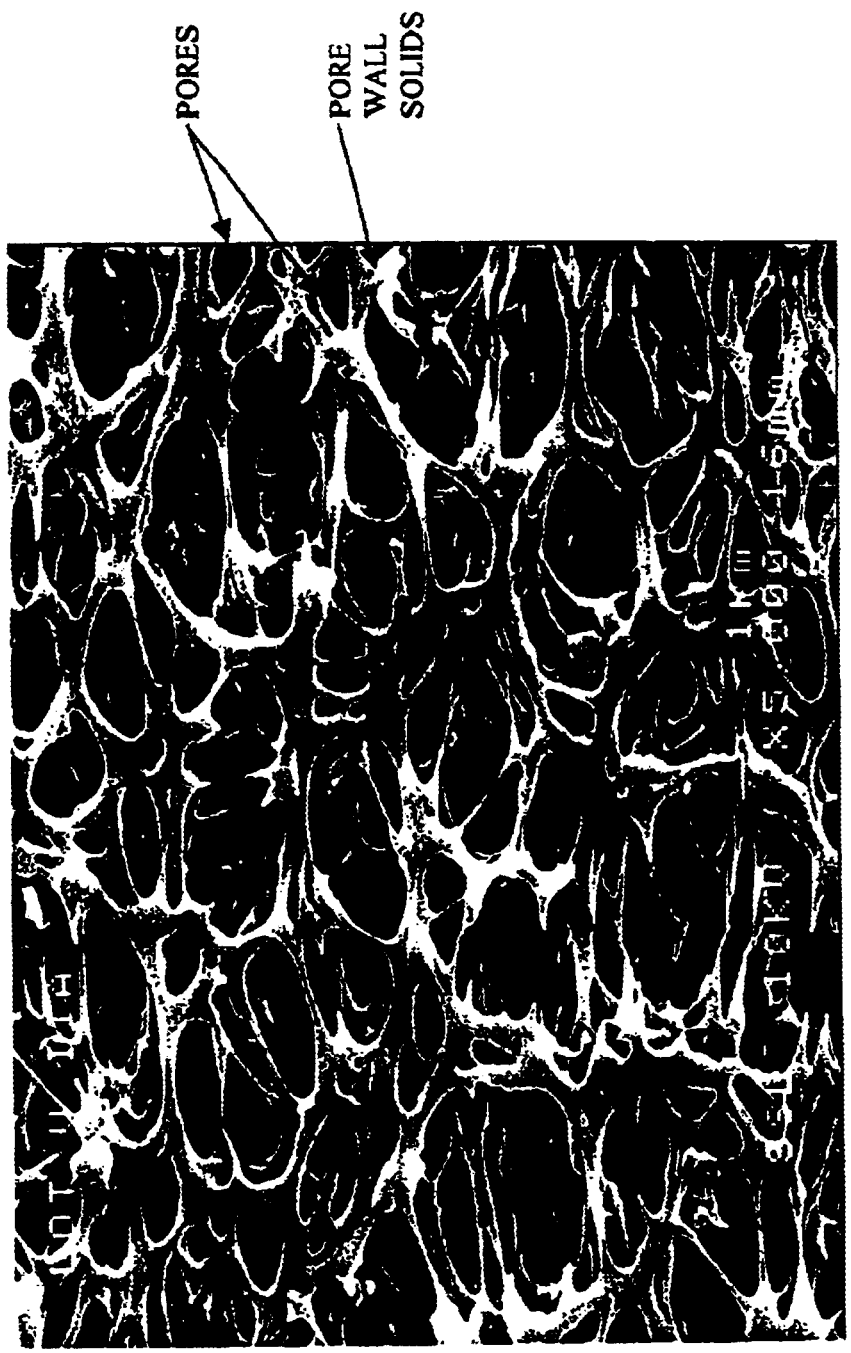
FIG. 3 shows a portion of a cross-section of a portion of the fiber at a magnification of 5,000 $\mu$m.

FIG. 3, a cross-section of Zone 1 at a magnification of 5,000 $\mu$m, shows pores and their boundary solid wall frames and the high uniformity of pore geometry and diverse irregular shapes of the individual pore dimensions. It is this high uniformity of pore size and high porosity as well as the thinness of Zone 1 which produces the high separation efficiency and high TMF of the membrane.

Figure 4:
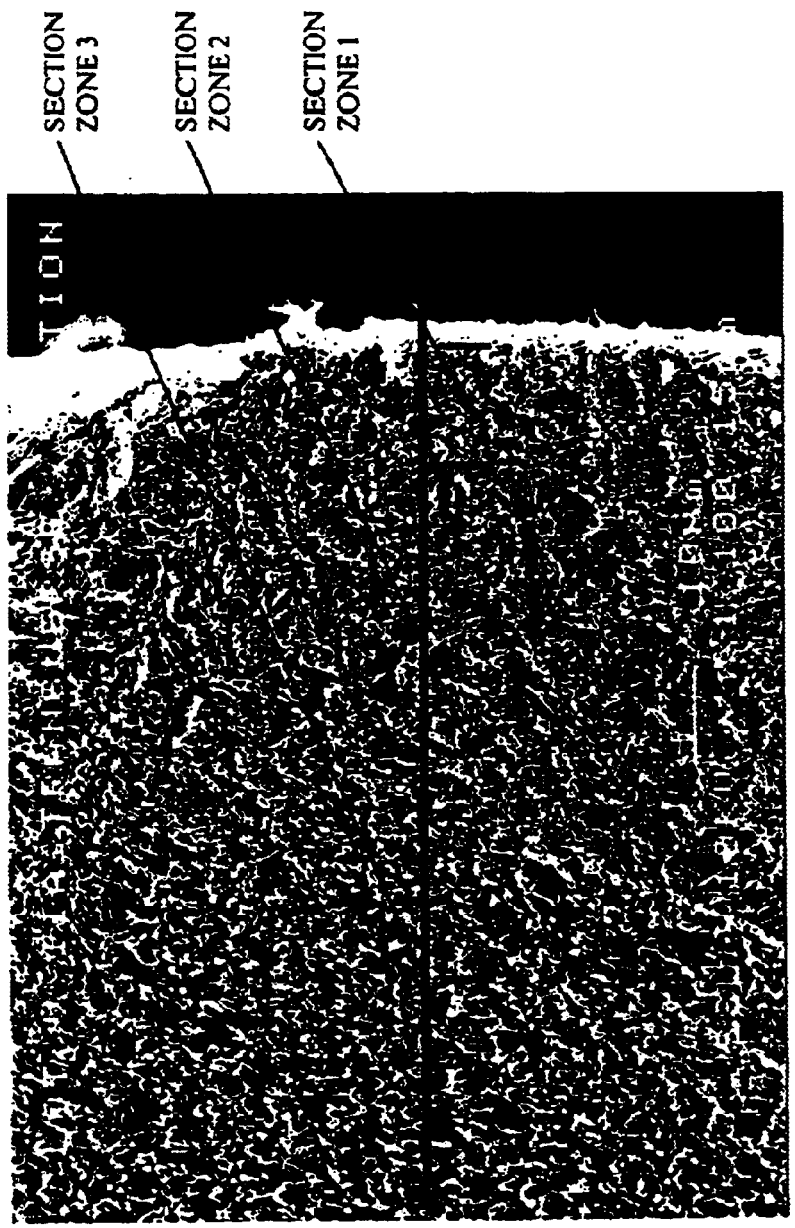
FIG. 4 is a SEM cross-section of Zones 1, 2 and 3 of the fiber shown in FIG. 2 at a magnification of 1,000 $\mu$m.

FIG. 4 shows a cross-section of Zones 1, 2 and 3 at a magnification of 1,0001 $\mu$m to illustrate the transition of the high-density structure of Zone 1 in comparison to the more open densities of Zones 2 and 3, as well as the uniformity and continuity of fiber structure producing high tensile and elongation strength.

Figure 5:
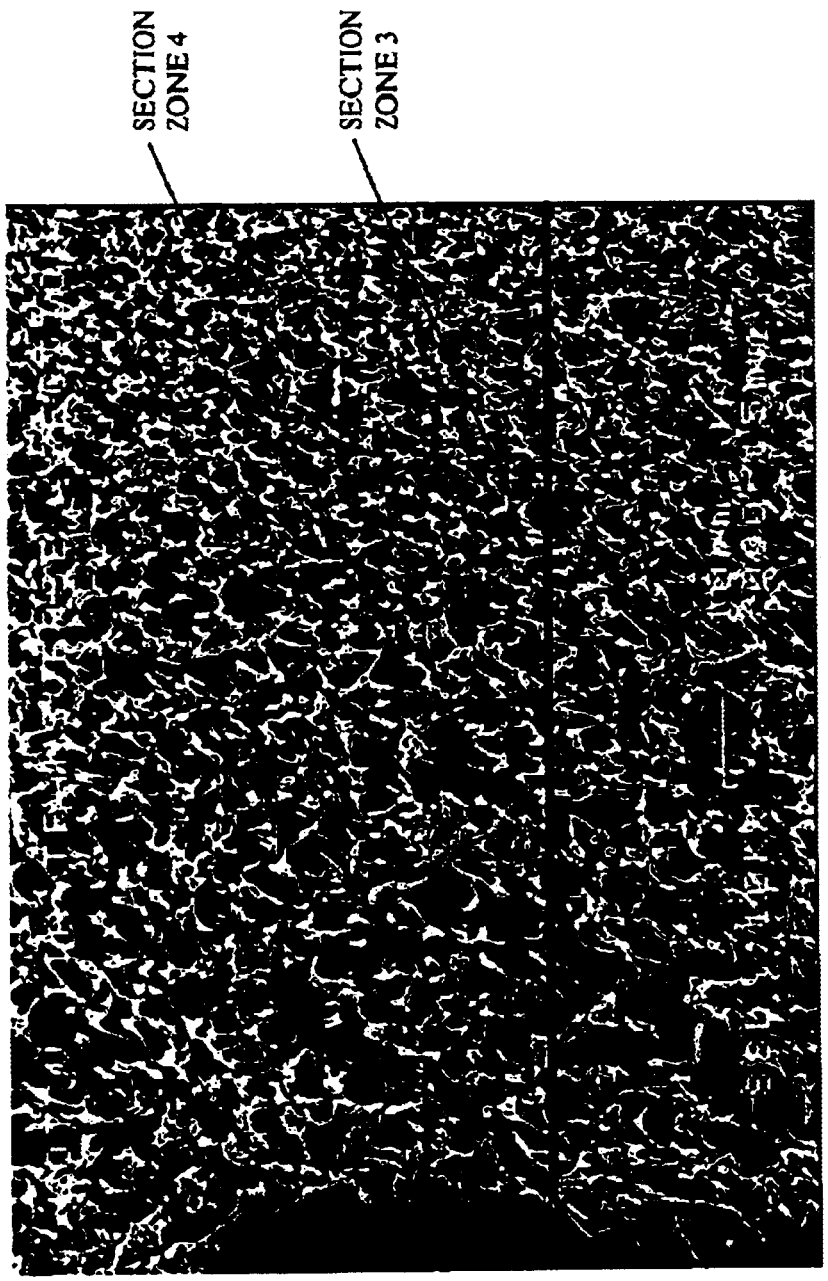
FIG. 5 is a SEM cross-section of Zones 3 and, 4 of the fiber shown in FIG. 2 at a magnification of 1,000 $\mu$m.

FIG. 5, also at a magnification of 1,000 $\mu$m, shows the structure of Zones 3 and 4 to illustrate the rapidly expanding open spaces and fluid communication channels which produce the lowered hydraulic resistance to flow of the exudate and results in a very high TMF as a finction of a very low TMP.

Figure 6:
FIG. 6 shows a transverse view of the inner lumen wall of the fiber at a magnification of 5,000 $\mu$m.

FIG. 6 is a 5,000 $\mu$m magnification of a transverse view of the inner lumen wall showing the highly open but contiguous nature of the structure at that site, facilitating fluid communication of the exudate from the flow through the fiber to the fiber lumen.

Figure 7:
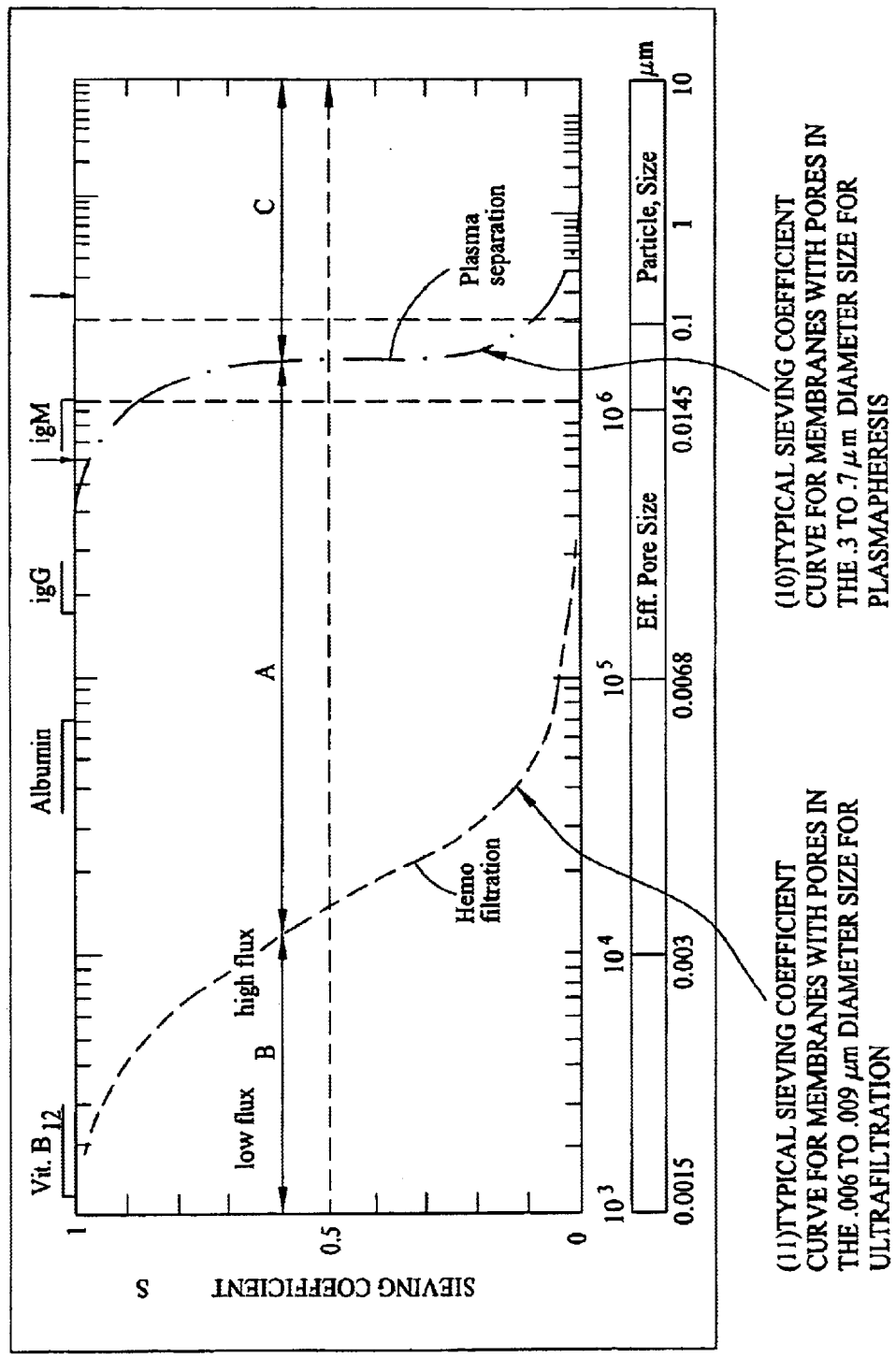
FIG. 7 is a graph illustrating the hollow fiber membrane sieving coefficient curves.

FIG. 7 illustrates a sieving coefficient curve to provide a measure of membrane performance in-situ in an operating environment. The sieving coefficient curves illustrated are determined or generated by measuring the amount of a series of specific solutes or proteins in exudate passed through the membrane by convection as a percentage of the amount of the permeate of the same solute or protein in the blood. The vertical axis of the chart illustrated is linear from 0 to 100% and the horizontal axis is semi-logarithmic in two scales; the first scale is expressed in pore size in $\mu$m; the second scale is expressed in the molecular weight of the solute in Daltons.

Curve 10 of FIG. 7 represents the typical curve of a plasma extraction membrane with exudate performance in Areas A and B. Curve 11 shows the typical exudate performance of a hemofilter (ultrafiltration) membrane with exudate performance in Area B, wherein Areas A plus B plus C constitute all components of the blood. Thus, Curve 10 represents the typical sieving coefficient curve for membranes with pores in the 0.3 to 0.7 $\mu$m diameter size, as used in plasmapheresis while Curve 11 represents a typical sieving coefficient curve for membranes with pores in the 0.006 to 0.009 $\mu$m diameter size used for ultrafiltration.

The driving force for convective transport of the plasma fluid and solutes is the TMF equal to $P_f \times TMP$ (and linear below the critical flow limit) where $P_f$ is the hydraulic permeability of the membrane, and:

$$P_f = (n\pi r_p^4)/(\tau \mu \Delta x) \text{ Where:}$$

($n$)=Porosity (number of pores/unit area)

($\pi$)=3.14159

($r_p$)=Pore radius (pore size)

($\tau$)=Tortuosity of path ($\mu$)=Viscosity of solution ($\Delta x$)=Membrane thickness It should be noted that the largest leverage to obtaining optimum TMF is the radius of the pores because it is raised to the fourth power. The next largest lever is the porosity or number of such point area and the effect of the pore radius which is multiplied by the porosity. Functional optimization for this application therefore also relies on achieving a tight standard deviation of pore radius in the effective zone of filtration as well as a high density of such pores in the primary filtration zone of the membrane. The relationship is also affected by temperature to the extent that temperature changes the value of the parameters including the viscosity of the solution.

The membranes of the present invention may be prepared using any suitable polymer fibers which will result in a hollow fiber membrane which meets the biocompatibility requirements' and properties of the invention. Such membrane materials and surfaces must be highly biocompatible and resist clotting, protein adhesion and detrimental interaction with immune system components. The structural strength of the hollow fiber membranes must be high enough to safely withstand implantation as well as the hydraulic and physical perturbations existing in the vena cava environment. Thus, the functional convection extraction efficiency of such hollow fibers must be suitable to meet clinical treatment requirements in the smallest possible size in order to fit within the vena cava without stress. The membranes also must be designed with a morphology optimize for blood flow on the outside of the fiber and ultrafiltrate on the inner lumen of the fiber. A number of potentially suitable polymer fiber membrane materials are described in the aforesaid patents including fibers produced from polyurethane, polypropylene, polyethersulfone, polycarbonate, nylon, polyimide and other synthetic resins known to those skilled in the art A preferred polymer is polysulfone membrane, and more preferably a polysulfone modified with a polyethylene oxide-polyethylene glycol copolymer. Such polysulfone fibers are produced in the presence of polymer dopes, core fluids, and coagulation fluids using processes including membrane spinning methods which achieve the desired product. Examples of such additive materials used in the polymerization process, spinning process and/or fiber membrane production include polyvinyl pyrrolidone, N-methyl pyrrolidone, dimethyl acetomide, dimethyl sulfoxide, and mixtures of two or more such materials. Such polysulfone fibers have been found to have the least detrimental characteristics that influence protein membrane interaction such as crystallinity, ionic groups, hydrogen bonding groups and hydrophobic sites. The specific method used for producing the aforesaid polymers as well: as the processes and parameters during the manufacture are known to those skilled in the art. The general specifications and variation range of parameters for the hollow fiber membranes for medical applications within the scope of the present invention are as follows:

PLASMAPHERESIS APPLICATIONS

| PARAMETER | SPECIFICATIONS | | RANGE OF APPLICATION | |
|---|---|---|---|---|
| | FROM | TO | FROM | TO |
| Outer Diameter μm | 735 | 765 | 200 | 800 |
| Inner Diameter μm | 240 | 260 | 50 | 700 |
| Wall Thickness μm | 175 | 260 | 50 | 600 |
| Zone 1 mean flow pore diameter μm | 0.7 | 0.8 | 0.3 | 1 |
| Zone 4 pores @ ID diameter μm | 5 | 40 | 1 | 60 |
| Tensile force @ Break Pounds/in$^2$ | 750 | 900 | 500 | 1500 |
| Elongation @ Break % | 65 | 80 | 50 | 150 |
| Fluid Flux (H$_2$O) ml/min/cm$^2$ @ 100 mmHg | 1.0 | 1.5 | 1.0 | 10 |
| TMF plasma ml/min/cm$^2$/10 mmHg | .75 | 4 | .5 | 9 |

ULTRAFILTRATION APPLICATIONS

| PARAMETER | SPECIFICATIONS | | RANGE OF APPLICATION | |
|---|---|---|---|---|
| | FROM | TO | FROM | TO |
| Outer Diameter μm | 450 | 650 | 123 | 750 |
| Inner Diameter μm | 250 | 325 | 100 | 700 |
| Wall Thickness μm | 150 | 200 | 40 | 400 |
| Zone 1 mean flow pore diameter μm | 0.01 | 0.03 | 0.005 | 0.05 |
| Zone 4 pore @ ID diameter μm | 5 | 40 | 1 | 60 |
| TMF H$_2$O ml/min/cm$^2$/10 mmHg | .75 | 4 | .5 | 9 |
| Tensile force @ Break Pounds/in$^2$ | 700 | 800 | 450 | 1200 |
| Elongation @ Break % | 50 | 65 | 40 | 100 |

Examples of medical applications for which the hollow fiber membranes of the present invention may be used include the following: therapeutic apheresis applications including plasma exchange, cascade protein separation by filtration, cascade protein removal or modification by adsorption cartridge, cryogenic modification, or chemical adaptation; fluid management application or congestive heart failure both acute and chronic; tissue engineering applications including online generation of media for bioreactor from xenogenic, allogenic, and autogenic sources; continuous renal replacement therapy (CRRT) for both acute and chronic kidney failure; edema prevention therapies for MODS (multiple organ dysfunction syndrome); cytokine removal or modification in therapy for septic shock or SIRS (systemic inflammatory response syndrome); plasma extraction from peritoneal ascites; intermittent hemodialysis (IS)) or hemodiafiltration; and ARDS (acute respiratory distress syndrome) therapy by reduction of pulmonary edema and physiological pulmonary dead space.

Additional uses for the specific membranes of the present invention as well as those covered in the aforesaid U.S. patents incorporated herein by reference will be evident to those skilled in the art.

What is claimed is:

1. A method of carrying out in-vivo plasmapheresis and/or in-vivo ultrafiltration of a patient's blood, comprising:
   implanting a filter device within a blood vessel of a patient, said filter device comprising a plurality of elongated hollow fibers each fiber having an outer wall, an inner wall and an interior lumen extending along the length thereof, and wherein the fiber wall structure is a continuous change in mass density from said outer wall to said inner wall and comprises a continuum of voids bounded by solid frames, said fiber wall having an asymmetrical pore size and asymmetrical mass density morphology between inner and outer fiber wall surfaces wherein the mass density adjacent to said outer wall is greater than the mass density adjacent to said inner wall, and passing blood plasma and toxins through said fiber wall from the outer wall surface to said interior lumen and directing said blood plasma and toxins from the patient through said interior lumen.

2. A method of claim 1 wherein said filter device includes a catheter in direct fluid communication with said interior lumen of said fibers, said method including directing said blood plasma and toxins from the patient through said catheter.

3. A method of carrying out in vivo plasmapheresis and/or in-vivo ultrafiltration of a patient's blood, comprising:
   implanting a filter device within a blood vessel of a patient, said filter device comprising a plurality of elongated hollow fibers each fiber having an outer wall, an inner wall and an interior lumen extending along the length thereof, and wherein the fiber wall structure is a continuous change in mass density from said outer wall to said inner wall and comprises a continuum of voids bounded by solid frames, said fiber wall having a plurality of zones between inner and outer wall surfaces, each of said zones having a mass density different than the mass density of an adjacent zone, said fiber wall characterized by having a lower mass density zone at the inner wall surface and a higher mass density zone at the outer wall surface and passing blood plasma and toxins through said fiber wall from the outer wall surface to said interior lumen and directing said blood plasma and toxins from the patient through said interior lumen.

4. A method of claim 3 wherein said filter device includes a catheter in direct fluid communication with said interior lumen of said fibers, said method including directing said blood plasma and toxins from the patient through said catheter.

5. A method of claim 3 wherein said membrane fiber wall has two mass density zones.

6. A method of claim 3 wherein said membrane fiber wall has three mass density zones.

7. A method of claim 3 wherein membrane fiber wall has four or more mass density zones.

8. A method of claim 3, 4, 5, 6 or 7 wherein each of said zones is characterized by a different average nominal pore size.

9. A method of claim 3 wherein said lower mass density zone is characterized by a nominal average pore diameter of between about 1 µm and about 60 µm.

10. A method of claim 3 wherein said higher mass density zone is characterized by a nominal average pore diameter of between about 0.3 µm and about 1 µm.

11. A method of claim 9 wherein said higher mass density zone is characterized by a nominal average pore diameter of between about 0.3 µm and about 1 µm.

12. A method of claim 3 comprising extracting at least 0.75 ml/min/cm$^2$/mm Hg of blood plasma at trans-membrane pressures of between about 5 mm Hg and about 20 mm Hg.

13. A method of claim 3 wherein said higher mass density zone is characterized by a nominal average pore diameter of between about 0.005 µm and about 0.05 µm.

14. A method of claim 9 wherein said higher mass density is characterized by a nominal average pore diameter of between about 0.005 µm and about 0.05 µm.

15. A method of claim 9 wherein said membrane has a plasma trans-membrane flux of between about 0.5 ml/min/cm$^2$ and about 9 ml/min/cm$^2$@ 10 mm Hg.

16. A method of claim 3 wherein said lower mass density is characterized by a nominal average pore diameter of between about 5 µm and about 40 µm.

17. A method of claim 16 wherein said higher mass density is characterized by a nominal average pore diameter of between about 0.7 µm and about 0.8 µm.

18. A method of claim 16 wherein said membrane has plasma trans-membrane flux of between 0.75 ml/min/cm$^2$ and about 4 ml/min/cm$^2$/@ 10 mm Hg.

19. A method of claim 16 wherein said higher mass density is characterized by a nominal average pore of between about 0.01 µm and about 0.03 µm.

20. A method of claim 3 wherein said membrane has a trans-membrane flux ($H_2O$) of between about 0.75 and about 4 ml/min/cm$^2$/@ 10 mm Hg.

21. A method of claim 1 wherein said fiber wall comprises a plurality of concentric circumferential zones between inner and outer wall surfaces, each of said circumferential zones comprising a continuous wall structure of pores and frames, wherein the mass density of adjacent concentric circumferential zones is different and wherein the mass density of said concentric circumferential zones decreases from said outer wall to said inner wall.

22. A method of claim 21 wherein said membrane fiber wall has two mass density zones.

23. A method of claim 21 wherein said membrane fiber wall has three mass density zones.

24. A method of claim 21 wherein membrane fiber wall has four or more mass density zones.

* * * * *